United States Patent [19]

Prochaska et al.

[11] Patent Number: 5,691,338
[45] Date of Patent: Nov. 25, 1997

[54] 1,2-DITHIOLE-3 THIONES FOR THE TREATMENT OF REVERSE TRANSCRIPTASE-DEPENDENT VIRAL INFECTIONS

[75] Inventors: Hans J. Prochaska; Bruce Polsky, both of New York, N.Y.

[73] Assignee: Sloan-Kettering Institute for Cancer Research, New York, N.Y.

[21] Appl. No.: 485,658

[22] Filed: Jun. 7, 1995

Related U.S. Application Data

[63] Continuation of Ser. No. 11,429, Jan. 29, 1993.
[51] Int. Cl.$^6$ ................................................. A61K 3/1495
[52] U.S. Cl. ........................ 514/252; 514/441; 514/262; 514/274
[58] Field of Search ................................. 514/252, 441, 514/262, 274

[56] References Cited

PUBLICATIONS

Roebuck, B.D., et al., Cancer Research 51:5501–5506 (1991). (Exhibit B).
Kensler, T.W., et al., Cancer Research 47:4271–4277 (1987). (Exhibit C).
Kong, X., et al., Antimicrobial Agents and ChemoTherapy 35(10):2003–2011. (Exhibit D); (1991).

DeClercq, E., AIDS Research And Human Retroviruses, 8(2):119–134. (Exhibit E). 1992.

Benson, A.B., Journal of Cellular Biochemistry, Supplement 17F: 278–291 (Aug. 1993). (Exhibit B).

CA117:165717; Chemical Abstract; STN OnLine 1991.

CA115:270158; Chemical Abstract; STN OnLine 1991.

*Primary Examiner*—Samuel Barts
*Attorney, Agent, or Firm*—John P. White

[57] ABSTRACT

This invention provides a method of inhibiting the replication of a reverse transcriptase-dependent virus in cells which comprises contacting infected cells with an effective amount of a 1,2-dithiole-3-thione. A composition for inhibiting reverse transcriptase-dependent viral replication of cells comprising an effective amount of a 1,2-dithiole-3-thione and a physiologically acceptable carrier is also provided.

15 Claims, 9 Drawing Sheets

OLTIPRAZ 1,2-DITHIOLE-3-THIONE

DIMETHYLFUMARATE tert-BUTYLHYDROQUINONE

1,2-DITHIOLE-3 THIONES FOR THE TREATMENT OF REVERSE TRANSCRIPTASE-DEPENDENT VIRAL INFECTIONS

This is a continuation of application Ser. No. 08/011,429, filed Jan. 29, 1993.

BACKGROUND OF THE INVENTION

Throughout this application, various publications are referenced by arabic numerals within parentheses. Full citations for these publications may be found at the end of the specification immediately preceding the claims. The disclosure of those publications in their entireties are hereby incorporated by reference into this application in order to more fully describe the state of the art as known to those skilled therein as of the date of the invention described and claimed.

Infection with the human immunodeficiency virus (HIV-1) results in a number of metabolic derangements concomitant with a striking loss of CD-4$^+$ cells. However, the mechanisms by which CD-4$^+$ cells are lost is still unclear.

Oxidative stress has received increasing attention as a mechanism for the pathogenesis of HIV-1 since publication of reports describing markedly lower reduced glutathione (GSH) levels in plasma and peripheral blood mononuclear cells of HIV-1-infected patients (1,2). GSH, which represents greater than 90% of cellular acid-soluble thiol pools, is a major antioxidant defense (3). The role of GSH in the pathogenesis of AIDS has been inferred by the following evidence (4): First, adequate GSH levels are required for a variety of vital immune functions. Second, GSH levels are decreased in asymptomatic as well as symptomatic HIV-1-infected patients (thus rendering it unlikely that cachexia is responsible for GSH loss). Third, the severity of GSH loss correlates with disease progression. Fourth, HIV-1 infection is associated with elevated levels of inflammatory cytokines which generate intracellular oxidants. Fifth, HIV-1 transcription in vitro is dramatically increased by inflammatory cytokines as well as by $H_2O_2$.

This hypothesis was tested in vitro by the administration of N-acetylcysteine (5,6) and the ester of GSH (6). These low molecular weight thiols were shown to effectively inhibit the replication of HIV-1 in chronically and acutely infected cells. The mechanism by which these thiols inhibit HIV-1 replication is believed to be due to their ability to inhibit the activation of Nuclear Factor κB under conditions of oxidative stress (7). There has been enthusiasm for testing compounds such as N-acetylcysteine or the ester of GSH in patients infected with HIV-1 (8,9). Since N-acetylcysteine and GSH inhibit HIV-1 replication in vitro, it has been hypothesized that inducers of endogenous GSH synthesis would be effective anti-HIV-1 agents.

Infection with the human immunodeficiency virus type-1 (HIV-1) results in a striking diminution of reduced glutathione (GSH) levels in peripheral blood mononuclear cells, plasma, and lung epithelial lining fluid. Moreover, supplementation of medium with either N-acetyl cysteine or esterified GSH can markedly decrease viral replication in cultured cells. Since certain compounds can protect rodents from the toxic and neoplastic effects of chemical carcinogens by elevating GSH and phase II enzyme levels, we wanted to compare the ability of these agents to induce GSH and quinone reductase (a Phase II enzyme) in H9 human cutaneous T-cell lymphoma cells with their competence to inhibit HIV-1 replication. Compounds such as oltipraz [4-methyl-5-(2-pyrazinyl)-1,2-dithiole-3-thione], 1,2-dithiole-3-thione, tert-butylhydroquinone, and dimethyl fumarate elevate the levels of GSH and quinone reductase in this cell line.

However, the results of this work demonstrate that the mechanism of the inhibiton of viral replication is unrelated to a 1,2-dithiole-3-thione's ability to induce GSH and is unexpectedly due to its ability to irreversibly inhibit reverse transcriptase (RT).

SUMMARY

This invention provides a method of inhibiting the replication of a reverse transcriptase-dependent virus which comprises contacting cells infected with the reverse transcriptase-dependent virus with an effective amount of a 1,2-dithiole-3-thione. This invention also provides a composition for inhibiting the replication of a reverse transcriptase-dependent virus in cells infected with the reverse transcriptase-dependent virus which comprises a physiologically acceptable carrier and an amount of an 1,2-dithiole-3-thione effective to inhibit replication of the reverse transcriptase-dependent virus.

Figure 1:
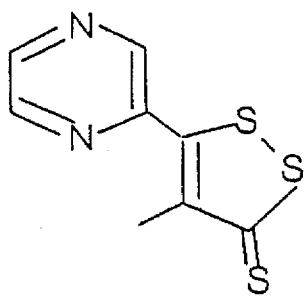
FIG. 1. Structures of GSH/Phase II enzyme inducers tested.
Figure 1:
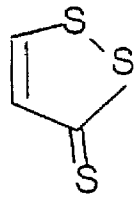
Figure 1:
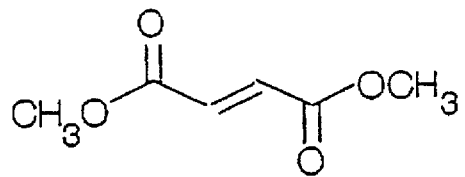
Figure 1:
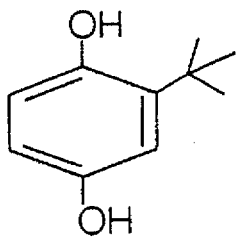

The $K_i$ values were determined from the secondary Segal transformations (Insets), which were generated from the Dixon plots (1/v vs [oltipraz]) as described (26). Note that oltipraz is a non-competitive inhibitor with respect to TTP ($K_i$=183±50 µM; N=2 experiments) and mixed with respect to poly(A):oligo(dT) ($K_i$=189±29 µM; N=3 experiments).

FIG. 6. Time- and concentration-dependent inhibition of HIV-1 reverse transcriptase (RT) by oltipraz in the presence of TTP (above) but not poly(A):oligo(dT) (below). RT was preincubated for the times indicated with oltipraz dissolved in DPBS containing 1 mg/ml bovine serum albumin, 0.13% DMSO, and either 4 µM TTP or 5 µg/ml poly(A):2.5 µg/ml oligo(dT). After incubation, 10 µl aliquots in triplicate were added to 25 µl of a reaction cocktail containing 4 µM TTP, 5 µg/ml poly(A), and 2.5 µg/ml oligo(dT) and assayed for TTP incorporation into DNA over 30 min. as described by Flexner, et al. (25). The insets are Kitz-Wilson transformations (41). Kinetic parameters for oltipraz in the presence of TTP for the experiment shown are $k_3$=0.0839 h$^{-1}$; $K_i$=15.6 µM. Kinetic parameters for oltipraz in the presence of poly(A):oligo(dT) are inconsistent with irreversible inhibition (i.e., the limiting rate of inactivation ($k_3$; represented by the y-intercept of the Kitz-Wilson plot) is a negative value).

Figure 7:
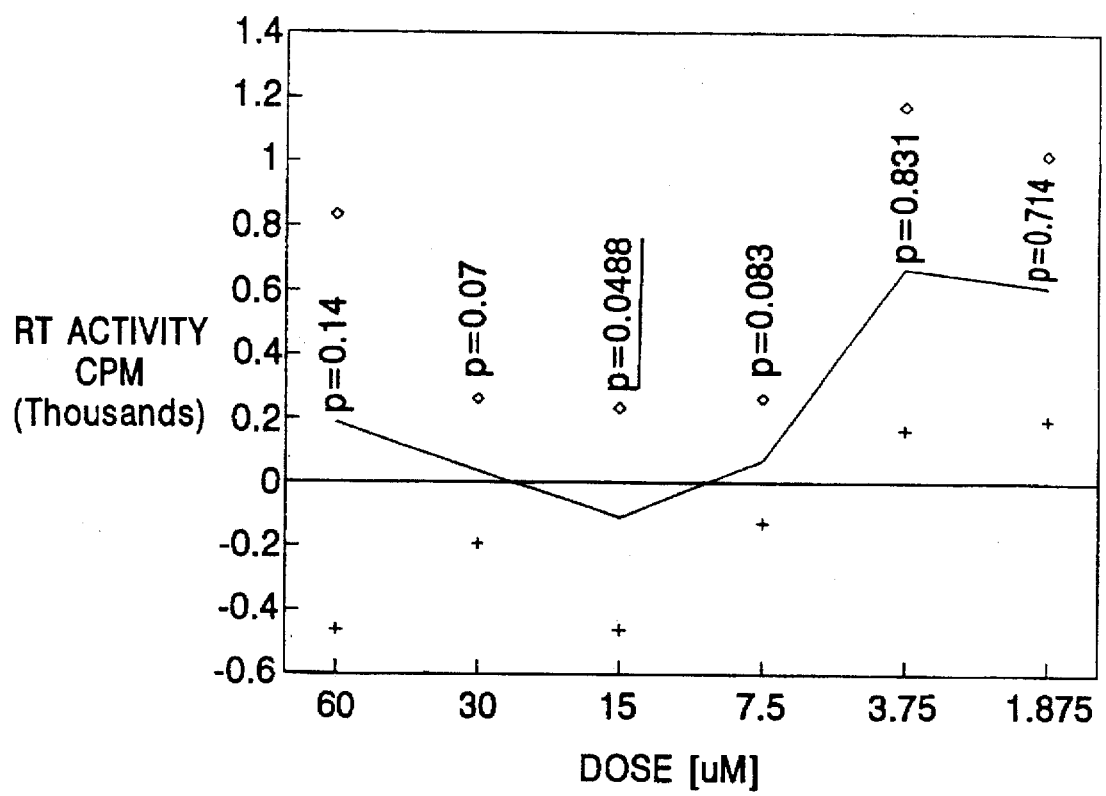

FIG. 7. Inhibition of HTLV-I reverse transcriptase activity from media of MT-2 (HTLV-I-infected) cells by Oltipraz [4-methyl-5-(2-pyrazinyl) -1,2-dithiole-3-thione] as described in Experimental Details.

DETAILED DESCRIPTION OF THE INVENTION

This invention provides a method of inhibiting the replication of a reverse transcriptase-dependent viruses, including retroviridae (human immunodeficiency virus-1, human immunodeficiency virus-2, HTLV-I, feline leukemia virus, feline immunodeficiency virus) and hepadnavirus (hepatitis B virus), which comprises contacting cells infected with a reverse transcriptase-dependent virus with an amount of a 1,2-dithiole-3-thione effective to inhibit replication of the virus. The 1,2-dithiole-3-thione has the following structure:

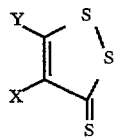

wherein X is a $C_1$–$C_5$ alkyl group or is —$CH_2COOR$, R being a $C_1$–$C_5$ alkyl group, and wherein Y is a 5- or 6-membered heterocyclic aromatic ring, 1–3 ring atoms of which are nitrogen, oxygen, or sulphur, the remaining ring atoms being carbon. In one embodiment of the invention, X is a methyl group and Y is 2-pyrazinyl (oltipraz) or 2-pyridazinyl. When X is methyl and Y is 2-pyrazinyl the effective concentration for inhibition of replication of human immunodeficiency virus-1 is in the range from about 2.0 µM to about 100.0 µM. In another embodiment of the invention X is methyl and Y is 2-thiofuranyl. In yet another embodiment of the invention, X is —$CH_2COOC_2H_5$ and Y is 3-pyrimidyl.

This invention also provides a method of inhibiting replication of human immunodeficiency virus-1 which comprises contacting virally infected cells with an amount of a 1,2-dithiole-3-thione and a second inhibitor of replication in amounts effective to inhibit replication. The second inhibitor can be, but is not limited to, 3'-azido-3'-deoxythymidine, 2',3'-dideoxyinosine, 2',3'-dideoxycytidine, or 2'3'-didehydro-3'-deoxythymidine. In the preferred embodiment of the invention the second inhibitor is 3'-azido-3'-deoxythymidine.

In one embodiment of the invention the infected cells are T-cells.

Further provided by this invention is a composition for inhibiting the replication of a reverse transcriptase-dependent virus, including retroviridae (human immunodeficiency virus-1, human immunodeficiency virus-2, HTLV-I, feline leukemia virus, feline immunodeficiency virus) and hepadnavirus (hepatitis B virus) in cells infected with a reverse transcriptase-dependent virus, which comprises a physiologically acceptable carrier and an amount of a 1,2-dithiole-3-thione effective to inhibit viral replication in the cells. The structure of the 1,2-dithiole-3-thione is shown above. In one embodiment of the invention X is methyl and Y is 2-pyrazinyl or 2-thiofuranyl. In yet another embodiment of this invention the composition further comprises a second inhibitor of replication of the reverse transcriptase-dependent virus. This second inhibitor may be, but is not limited to, 3'-azido-3'-deoxythymidine, 2'3'-dideoxyinosine, 2',3'-dideoxycytidine, or 2',3'-didehydro-3'-deoxythymidine.

For purposes of this invention, "physiologically acceptable carrier" means any of the standard pharmaceutical carriers. Examples of suitable carriers are well known in the art and may include, but are not limited to, any of the standard pharmaceutical carriers.

EXPERIMENTAL DETAILS

Materials and Methods

Oltipraz and 1,2-dithiole-3-thione were generous gifts of Professor Thomas W. Kensler of the Johns Hopkins School of Hygiene and Public Health. Dimethyl fumarate, tert-butylhydroquinone, and Ellman's reagent were purchased from Aldrich (Milwaukee, Wis.). tert-Butylhydroquinone was crystallized from ethyl acetate (19). Test compounds were dissolved as 1000–2000×stocks in dimethylsulfoxide (DMSO) and were stored at −20° C. until used. Thymidine-5'-triphosphate (TTP), GSH, 3-(4,5-dimethylthiazo-2-yl)-2,5-diphenyltetrazolium bromide, Tween 20, Triton X-100, bovine serum albumin (type V), NADP$^+$, glucose 6-phosphate, baker's yeast glucose-6-phosphate dehydrogenase, Tris, and menadione were obtained from Sigma (St. Louis, Mo.). Bradford reagent was obtained from Bio-Rad (Richmond, Calif.). 3'-Azido-3'-deoxythymidine (AZT) and 3'-azido-3'-deoxythymidine-5'-triphosphate (AZT triphosphate) were obtained from Burroughs-Wellcome (Research Triangle Park, N.C.) and Moravek Biochemicals (Brea, Calif.), respectively. Poly(A) and oligo (dT) (n=10) were obtained from Pharmacia (Piscataway, N.J.). $^{32}$p TTP (800 Ci/mmole) was purchased from New England Nuclear Research Products (Boston, Mass.) and p24 Enzyme-linked immunosorbent assay kits were purchased from Coulter Immunology (Hialeah, Fla.). Recombinant HIV-1 reverse transcriptase (RT) was obtained from Worthington (Freehold, N.J.). DE81 paper was obtained from Whatman (Maidstone, UK). 96-well U- and flat-bottomed plates were obtained from Falcon (Becton-Dickinson Labware, Oxnard, Calif.), and 96-well "half-area" (0.16 cm$^2$/well) plates were obtained from Co-star (Cambridge, Mass.). T-flasks were purchased from Corning (Corning, N.Y.). Centricon-10 microconcentrators were purchased from Amicon (Danvers, Mass.). For our IFA (immunofluorescent antibody assay directed against HIV-1), goat anti-human IgG-Fluorescein isothiocyanate conjugates were obtained from ICN Biomedical (Costa Mesa, Calif.), antisera directed against HIV-1 was obtained from our patient population, and 12-well HTC supercured 5 mm slides were obtained from Cell Line Associates (Newfield, N.J.). Other reagents, including spectral-grade dimethylsulfoxide (DMSO), were obtained from Fisher (Fair Lawn, N.J.). H9 human cutaneous T-cells and HIV-1 (HTLV$_{IIIB}$) were obtained from R. Gallo (National Cancer Institute, Bethesda, Md.). Cells were grown in RPMI 1640 containing 20% fetal calf serum supplemented with 100 U/ml penicillin and 100 µg/ml streptomycin (prepared by CORE media lab of the Memorial-Sloan Kettering Cancer Center).

Determination of GSH and QR Levels Grown in Flasks

Five ml of medium was added to T-25 flasks and DMSO containing tests compounds were added to a final concentration of 0.1%. Control medium contained 0.1% DMSO. After the drugs were added, $5 \times 10^6$ cells in 5 ml of medium was added to each T-25 flask. The cells were grown at 37° C. in a humidified incubator supplemented with 5% $CO_2$ until harvested (N=3 flasks/group). At the indicated times, cells were isolated by centrifugation ($500 \times g \times 10$ min) and were washed three times by adding 10 ml of ice-cold DPBS, mixing, and centrifuging in a refrigerated centrifuge ($500 \times g \times 10$ min) to isolate the cell pellets. The cells were then lysed by the addition of 400 µl of ice-cold DPBS containing 0.5% Triton X-100 and vortexing. Supernatants were then isolated by centrifuging the lysates ($5000 \times g \times 20$ min). Samples were kept on ice or refrigerated until the reagents for QR or GSH spectrophotometric assays were added to the aliquoted microtiter plates. QR levels were determined by aliquoting 10 µl/well of supernatant in a 96-well plate and measuring the activity by the assay described by Prochaska and Santamaria (20) except that the final NADP$^+$ concentration was 200 µM (21). Samples were assayed in quadruplicate, and dicoumarol inhibitable-rates (which generally represented less than 5% of the total rate) were also measured. Spectrophotometric blanks contained 10 µl of DPBS with 0.5% Triton X-100. For the GSH assay, 300 µl of sample was placed in a centricon-10 microconcentrator and centrifuged ($5000 \times g \times 45$ min) until enough ultrafiltrate could be collected. 50 µl/well of sample in quadruplicate was placed in a 96 well "half-area" plate after which 20 µl of 1 mM Ellman's reagent dissolved in DPBS was added. The yellow color (22) developed within 5 min and was scanned with a uv$_{max}$ microtiter scanner (Palo Alto, Calif.) at 405 nm. Spectrophotometric blanks contained 50 µl DPBS with 0.5% Triton X-100 and 20 µl of 1 mM Ellman's reagent in DPBS. The optical densities of the specimens were calibrated to a GSH standard curve. Protein contents were determined in 3 ml cuvettes by the Bradford method (23). The protein content in the ultrafiltrates employed for GSH determinations were negligible (<0.01 mg/ml).

Determination of QR levels in microtiter wells

We confirmed that the induction of QR in microtiter wells mirrored our results in T-25 flasks by using the method of Prochaska and Santamaria (20). Medium (100 µl) containing 0.1% final concentration DMSO was added to all wells except columns designated to contain the highest concentration of drug or spectrophotometric blanks in duplicate sets of U-bottomed microtiter plates. 200 µl of media containing drug (final DMSO concentration=0.1%) was added to the empty column of wells and then diluted in 2-fold serial dilutions across. After the serial dilutions were performed, 100 µl of media containing $1 \times 10^6$ cells/ml was added to each well, and the plates were placed in a 37° C. incubator for 48 h. One set of plates was assayed as described (21) for QR activity, the other was assayed for cell number by the method for Alley et al. (24).

Assay of HIV-1 replication

The effects for test compounds were assessed by means of both IFA and p24 release. In general, the following protocol was followed: H9 cells were infected with HIV-1 at 1000 50% infective doses of viruses/$10^6$ cells. Virus was allowed to adsorb for 1 h, after which unadsorbed virus was removed by centrifugation. The cells were resuspended and washed twice with PBS (without Ca$^{+2}$ or Mg$^{+2}$ salts) and centrifuged to collect the cell pellet ($150 \times g \times 10$ min). Cells were suspended in fresh medium and added at a final cell density of 500,000 cells/ml in a 96-well plate with media containing 0.1% DMSO and various concentrations of test compounds. The cells were re-fed freshly prepared media containing 0.1% DMSO±test compounds on day four (for preinduction experiments, cells were exposed to inducers on days −2, 0, and +4 days relative to infection). After seven days, cells were examined for cytoxicity by trypan blue exclusion, the degree of infection with HIV-1 by IFA, and the supernatants were assayed for p24 levels according to the manufacturer's directions. The IFA procedure can be summarized as follows: The cells were washed twice in PBS and were placed in 5 mm 12-well slides. After allowing the slides to dry and fixing the cells with acetone for 5 min, 10 µl of HIV-1 positive serum in 40 µl PBS was added to each well and allowed to incubate at 37° C. for 30 min. After incubation, the slides were washed twice with PBS and incubated at 37° C. for 30 min with 2.5 µl goat anti-human IgG-fluorescein isothiocyanate conjugate in 50 µl PBS containing 0.01% Evans Blue per well. The slides were then washed twice with PBS, dried, and mounted with 50% glycerol in PBS, and scored for the percentage of fluorescent cells by fluorescent microscopy.

Assay of reverse transcriptase

Reverse transcriptase assays were performed as described by Flexner, et al. (25) using recombinant HIV-1 RT as the source of enzyme. Dilutions and assay were carried out in 96-well "half-area" plates. The enzyme with various concentrations of test compounds were dissolved in DPBS containing 1% w/v BSA and diluted in 50 µl volumes; 10 µl aliquots in triplicate were transferred to another plate for the enzyme assay. The reactions were initiated by the addition of 25 µl/well of buffer containing 50 mM Tris•Cl (pH 8.0), 75 mM KCl, 1 mM dithiothreitol, 2 mM MgCl$_2$, 5 µg/ml poly(A), 2.5 µg/ml oligo (dT), 10 µCi/ml $^{32}$P TTP with or without unlabeled TTP. Unlabeled TTP was used in $K_i$ determinations and in experiments evaluating the effects of oltipraz and AZT triphosphate alone or in combination. The plates were incubated at 37° C. for 60 minutes except for $K_i$ and synergy experiments (30 min). TTP incorporation was measured by spotting 20 µl of the reaction cocktail onto DE81 paper, washing the paper with 4×5 min washes of 300 mM NaCl and 30 mM sodium citrate (pH 7.0), drying the paper, and counting the paper by liquid scintillation counting. The assays performed with oltipraz and 1,2-dithiole-3-thione contained 0.29% final concentration DMSO. This concentration of DMSO had no effect on RT activity.

Data analysis and statistical methods

Statistical significance for GSH and QR levels were established by the unpaired t test using the INSTAT statistics program (Graphpad, San Diego, Calif.). The $K_i$ of oltipraz was determined by performing Segal transformations (26) of Dixon plots. The dose-effect relationships of oltipraz and AZT, alone or in combination, were determined by the median effect method of Chou and Talalay (27). Calculations were performed on spreadsheets using Lotus 1-2-3 software (Cambridge, Mass.).

Detection of inhibitors of HTLV-I reverse transcriptase using MT-2 cells

MT-2 is a lymphocytic cell-line that is transformed by, and is antigen positive for HTLV-I. HTLV-I can be detected in supernatants of MT-2 cultures by monitoring reverse transcriptase activity. Using the MT-2 system compounds that are inhibitors of HTLV-I reverse transciptase can be identified. MT-2 cells are washed and incubated in triplicate with various concentrations of the test compounds, positive drug controls, negative drug controls or media alone. A cell-line that is negative for HTLV-I, such as H9, is used as a negative reverse transcriptase control. After 72 hours of incubation, culture supernatants are harvested and tested for reverse transcriptase activity as described (25). Inhibition of reverse transcriptase activity is calculated by comparing the radioactive counts in the experimental compounds to the MT-2 non-drug controls. ED50's can be calculated for each compound.

RESULTS

EXAMPLES

Example 1

Induction of GSH and QR levels in H9 Cutaneous T-cell Lymphoma Cells

Figure 2A:
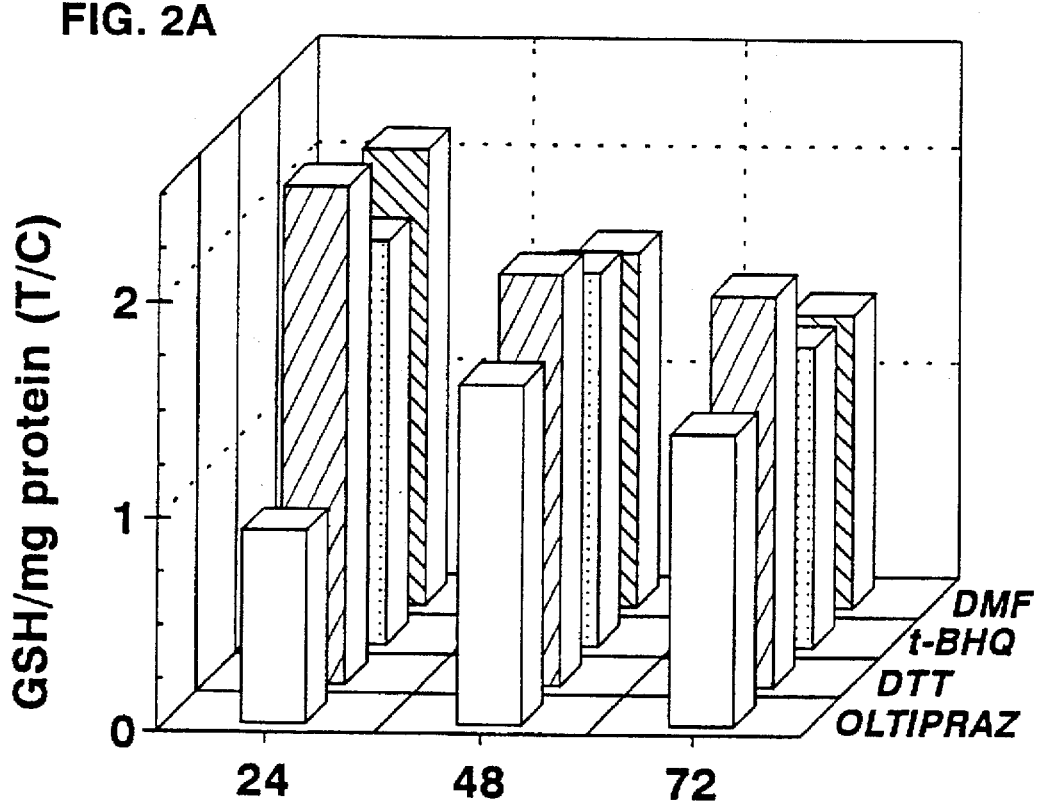
FIG. 2. Elevation of GSH (above) and QR (below) by 120 μM oltipraz, 120 μM, 1,2-dithiole-3-thione (DTT), 30 μM tert-butylhydroquinone (tBHQ), and 30 μM dimethyl fumarate (DMF). H9 cells were maintained in culture as described in Experimental Details. At zero time, $5 \times 10^6$ cells in 5 ml of medium were mixed with 5 ml of media containing 0.1% DMSO±test compounds. Cells were returned to the incubator until the times indicated above, and were processed for GSH and QR content as described in Experimental Details. Standard errors and control values are similar in magnitude as shown in Tables 1 and 2. All values shown are significantly greater than control (p<0.05) except for the GSH and QR levels in cells treated with oltipraz for 24 h (p=0.439 and 0.183, respectively) and GSH levels in cells treated with DMF for 72 h (p=0.0566).
Figure 2B:
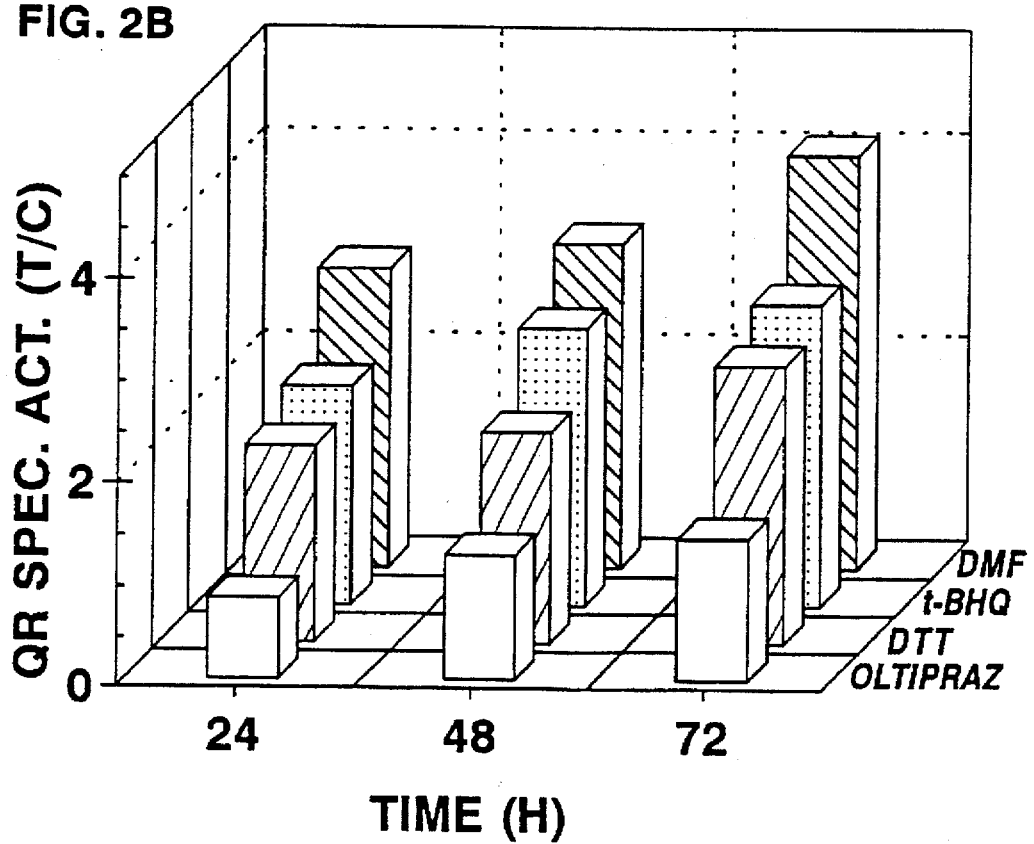

Prototypical anticarcinogenic enzyme inducers such as tert-butylhydroquinone, oltipraz, dimethyl fumarate, and 1,2-dithiole-3-thione (10,11) were evaluated in this study as inducers of QR and GSH in H9 cells (FIG. 1). These compounds were able to elevate both GSH and QR levels in a dose-dependent (Tables 1 and 2) and time-dependent fashion (Tables 1 and 2; FIG. 2). In general, oltipraz was the least effective inducer of QR and GSH, and in contrast with the other compounds tested, an apparent dissociation in GSH and QR levels was noted (i.e., QR increases were lower than the elevation of GSH). Moreover, there was greater interexperimental variation of the induction of GSH by oltipraz at earlier (24 h) and later (>72 h) time points than with the other compounds (data not shown). The levels of GSH and QR induction observed in H9 cells were very similar to those found in Hepa 1c1c7 murine hepatoma cells (28,29) and in primary murine marrow cells (30). The degree of induction of QR in cells grown in microtiter wells were identical to those grown in T-flasks, indicating that induction was not influenced by the geometry of the tissue culture container (data not shown). Bifunctional inducers (29), which require intact Ah receptor function, are inactive in H9 cells (data not shown).

TABLE 1

Elevation of glutathione levels (GSH) by 1,2-dithiole-3-thione and oltipraz in H9 cells. H9 cells were treated with either 1,2-dithiole-3-thione or oltipraz at the concentrations indicated and assayed as described in Experimental Procedures. All media contained 0.05% DMSO final concentration. Values in parentheses represent treated to control values.

| Treatment | Time (h) | Glutathione Levels (nmol/mg) Dose [μM] | | | |
| --- | --- | --- | --- | --- | --- |
| | | 0 | 30 | 60 | 120 |
| 1,2-dithiole-3-thione | 48 | 45.8 ± 1.1 | 53.5 ± 7.1 (1.17) | 57.5 ± 1.3** (1.26) | 74.9 ± 3.6* (1.63) |
| | 96 | 50.8 ± 1.6 | 59.4 ± 1.4* (1.17) | 65.0 ± 2.1** (1.71) | 109 ± 28* (2.15) |
| Oltipraz | 24 | 56.4 ± 0.85 | 62.0 ± 2.0 (1.10) | 83.5 ± 1.7*** (1.48) | 109 ± 28*** (1.93) |
| | 48 | 34.6 ± 2.5 | 52.7 ± 2.9** (1.52) | 68.0 ± 2.9** (1.96) | 79.7 ± 0.28*** (2.28) |
| | 72 | 47.0 ± 1.9 | 40.4 ± 4.7 (0.86) | 47.3 ± 4.6 (1.01) | 75.0 ± 8.6* (1.60) |

*p < 0.05; p < 0.01; *p < 0.001;

TABLE 2

Elevation of quinone reductase (QR) by 1,2-dithiole-3-thione and oltipraz in H9 cells. H9 cells were treated with either 1,2-dithiole-3-thione or oltipraz at the concentrations indicated and assayed as described in Experimental Procedures. All media contained 0.05% DMSO final concentration. Values in parentheses represent treated to control values.

| Treatment | Time (h) | Quinone Reductase Specific Activity (nmol/min/mg) Dose [μM] | | | |
| --- | --- | --- | --- | --- | --- |
| | | 0 | 30 | 60 | 120 |
| 1,2-dithiole-3-thione | 48 | 144 ± 2.6 | 232 ± 16** (1.61) | 244 ± 12.1*** (1.67) | 299 ± 11** (2.07) |
| | 96 | 50.8 ± 1.6 | 59.4 ± 1.4* | 65.0 ± 2.1** | 109 ± 28* |

TABLE 2-continued

Elevation of quinone reductase (QR) by 1,2-dithiole-3-thione and oltipraz in H9 cells. H9 cells were treated with either 1,2-dithiole-3-thione or oltipraz at the concentrations indicated and assayed as described in Experimental Procedures. All media contained 0.05% DMSO final concentration. Values in parentheses represent treated to control values.

| Treatment | Time (h) | Quinone Reductase Specific Activity (nmol/min/mg) Dose [µM] | | | |
|---|---|---|---|---|---|
| | | 0 | 30 | 60 | 120 |
| Oltipraz | 24 | 56.4 ± 0.85 | (1.17) 62.0 ± 2.0 | (1.71) 83.5 ± 1.7*** | (2.15) 109 ± 28** |
| | 48 | 34.6 ± 2.5 | (1.10) 52.7 ± 2.9** | (1.48) 68.0 ± 2.9** | (1.93) 79.7 ± 0.28*** |
| | 72 | 47.0 ± 1.9 | (1.52) 40.4 ± 4.7 (0.86) | (1.96) 47.3 ± 4.6 (1.01) | (2.28) 75.0 ± 8.6* (1.60) |

*p < 0.5; p < 0.01; *p < 0.001;

Example 2

Anticarcinogenic Enzyme Inducers as Inhibitors of HIV-1 Replication

Figure 3:
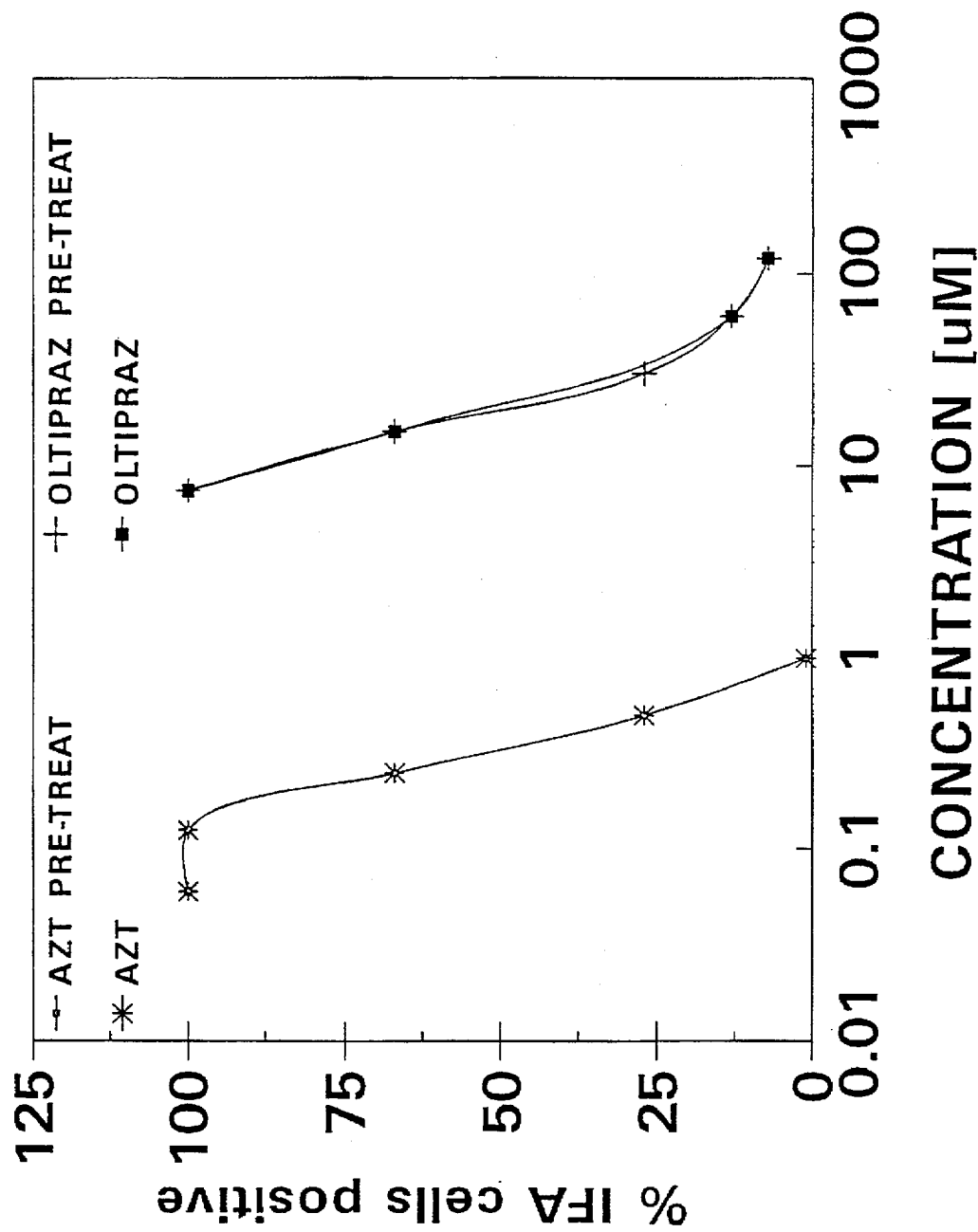
FIG. 3. Concentration-dependence of inhibition of HIV-1 replication by oltipraz and AZT. H9 cells were grown, exposed to inhibitors and virus as described in Experimental Details.

Our initial screen of anticarcinogenic enzyme inducers as inhibitors of HIV-1 replication revealed that only oltipraz was effective. The $IC_{50}$ as determined by IFA (9.7±2.0 µM; N=9 experiments) and p24 antigen release assays (14.8±3.1 µM; N=3 experiments) involving oltipraz were similar. Typical results are shown in FIG. 3. tert-Butylhydroquinone (up to 30 µM), 1,2-dithiole-3-thione (up to 120 µM), and dimethyl fumarate (up to 60 µM) were inactive at optimal inductive and non-cytotoxic doses. The inhibitory potency of oltipraz was approximately 100-fold less than that of AZT (FIG. 3). The pre-treatment of H9 cells with inducing agents 3–4 days prior to exposure to virus did not increase the antiviral effect of oltipraz, and the other compounds tested remained inactive (FIG. 3). Concentrations up to 120 µM oltipraz were non-cytotoxic.

Example 3

Effect of AZT and oltipraz in combination on HIV-1 replication

Figure 4A:
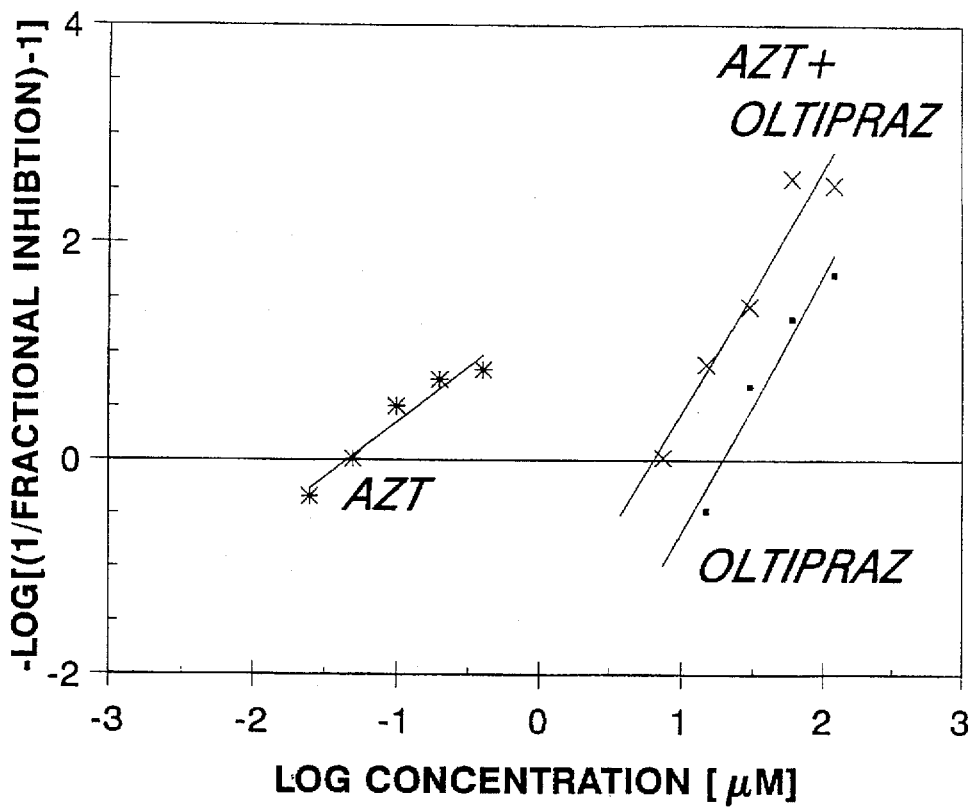
FIG. 4. Median effect plot (27) showing the inhibition of p24 release from H9 human cutaneous T-cell lymphoma cells by azidothymidine (AZT), oltipraz, or their mixture (1:300 ratio). $r^2$ for all plots are >0.94. The Inset is a graphical representation of the drug combination index with respect to fractional decrease of p24 production relative to HIV-1-infected controls, assuming that the drugs act in a mutually exclusive manner. Note that the drugs are synergistic with fractional inhibitions greater than 0.37. Calculation of the combination index assuming mutually non-exclusive conditions shows synergy with fractional inhibitions greater 0.46 (data not shown).
Figure 4B:
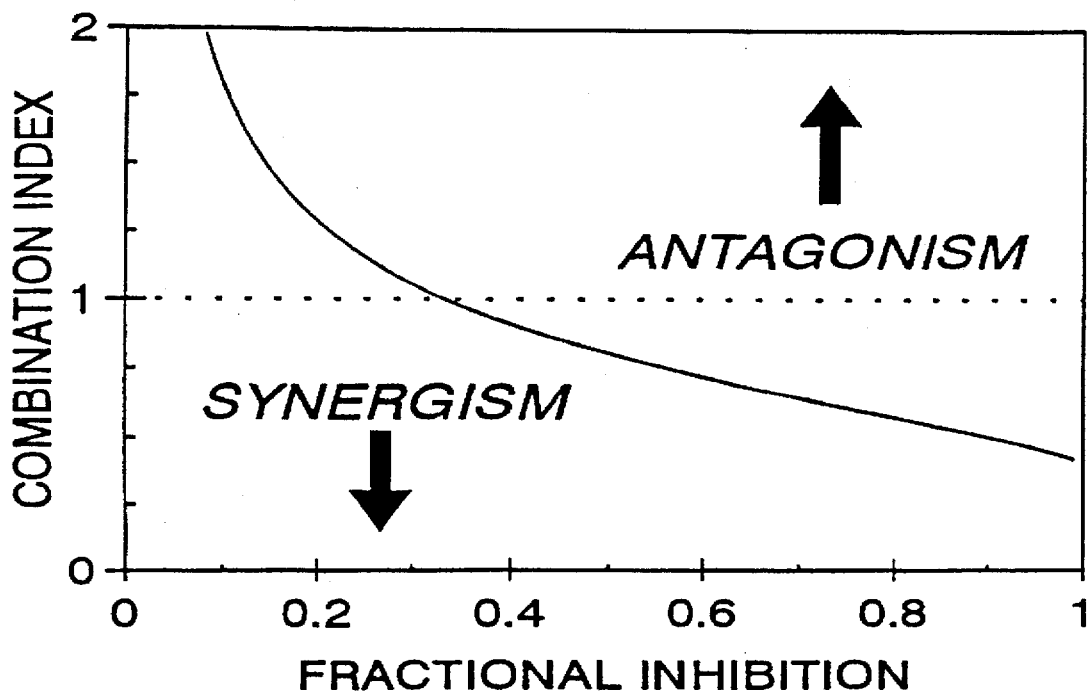
Figure 5A:
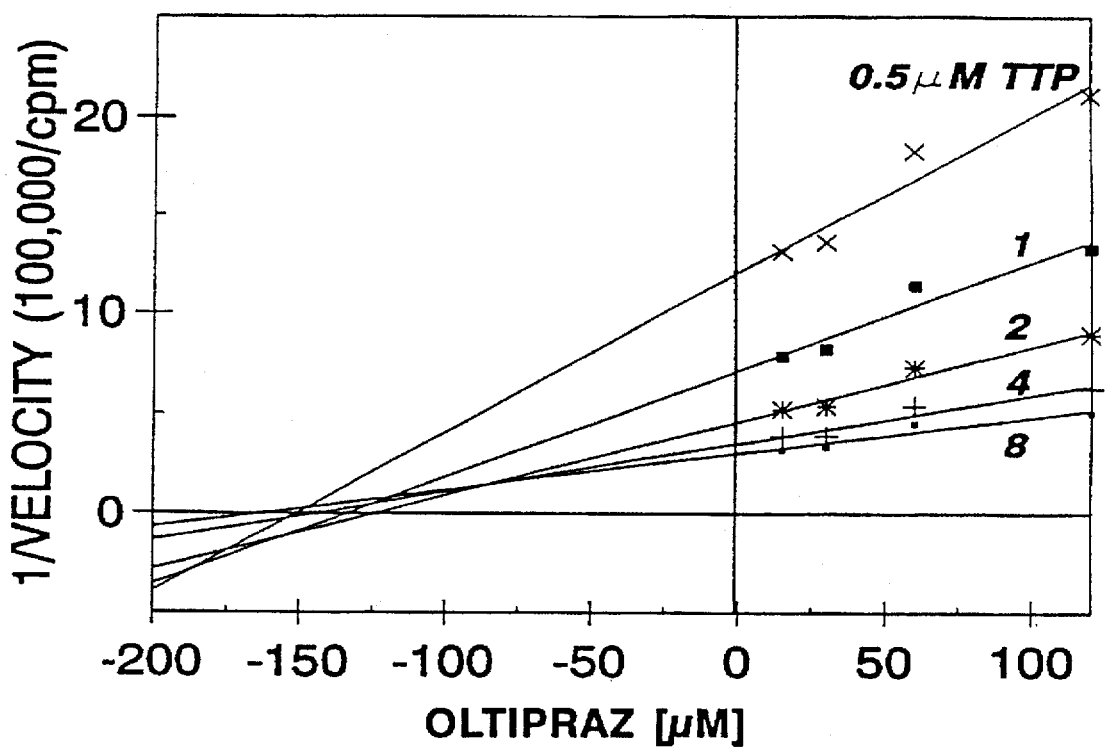
FIG. 5. Inhibition by oltipraz of HIV-1 reverse transcriptase with respect to TTP (above) and poly(A):oligo(dT) (below). Rates of TTP incorporation into the DNA were measured as described in Experimental Details with a range of concentrations of oltipraz with either (above) fixed concentrations of TTP in the presence of 5 μg/ml of poly(A) and 2.5 μg/ml of oligo (dT) or (below) fixed concentrations of a 2:1 ratio of poly(A):oligo(dT) in the presence of 4 μM TTP.
Figure 5B:
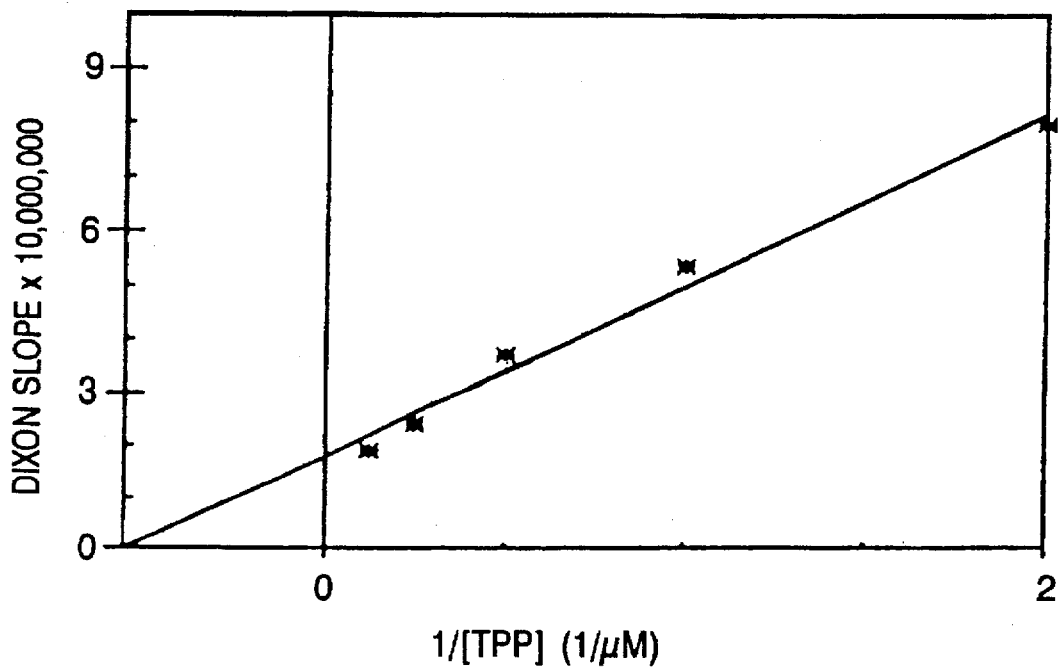
Figure 5C:
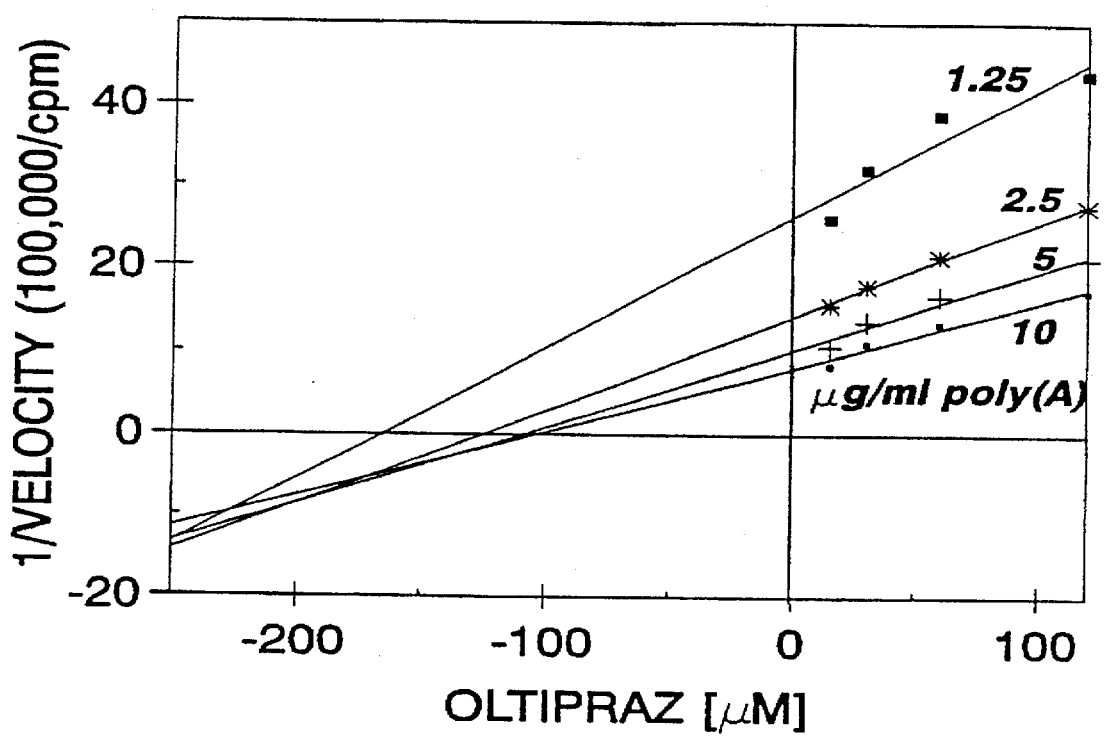
Figure 5D:
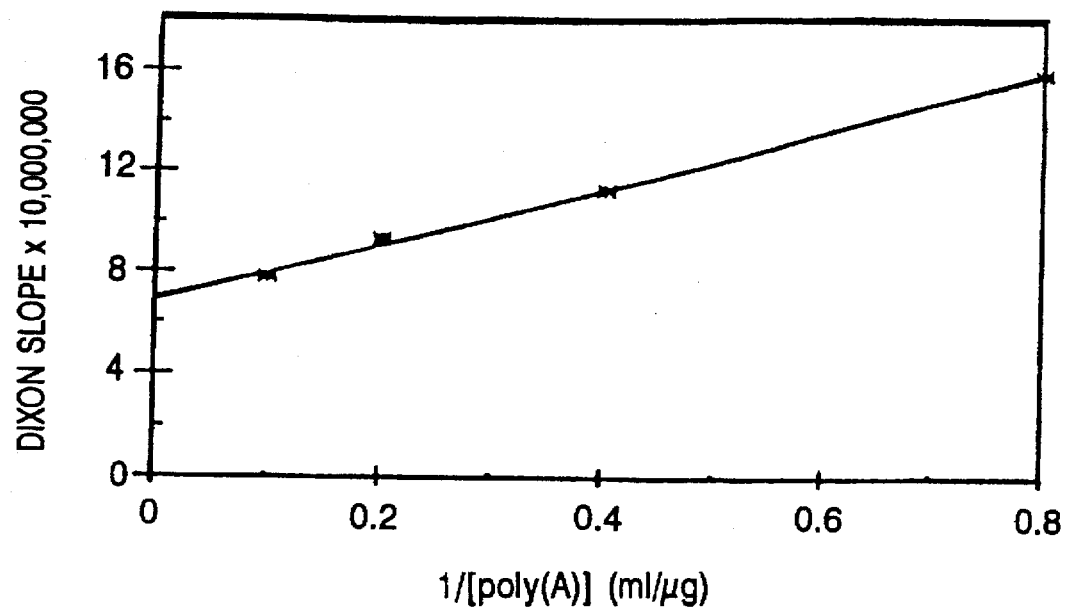
Figure 6A:
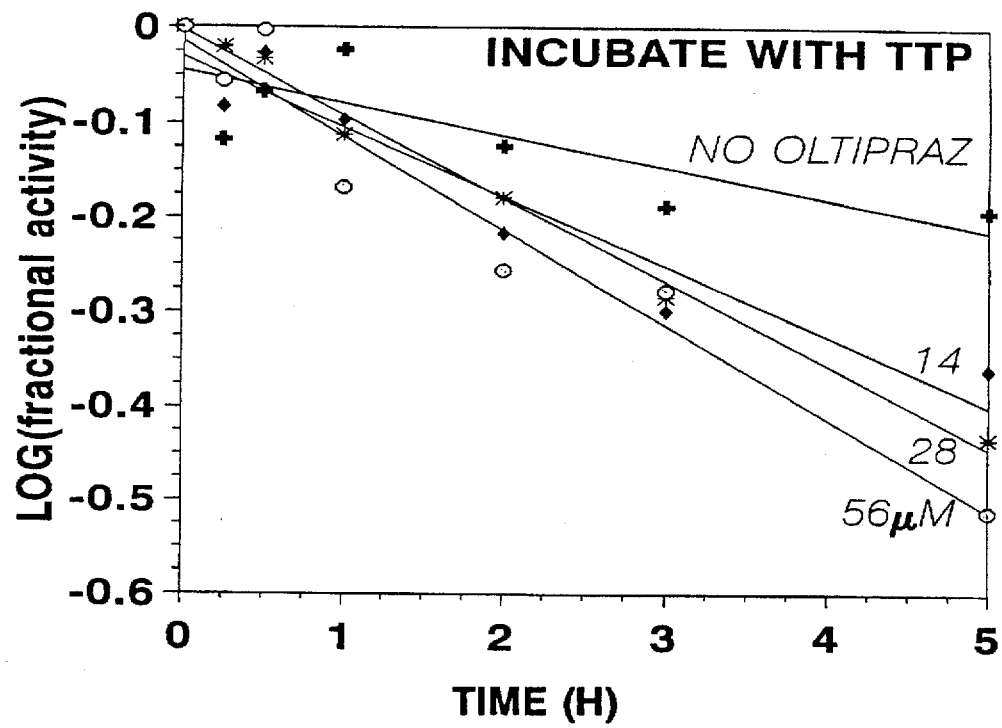
Figure 6B:
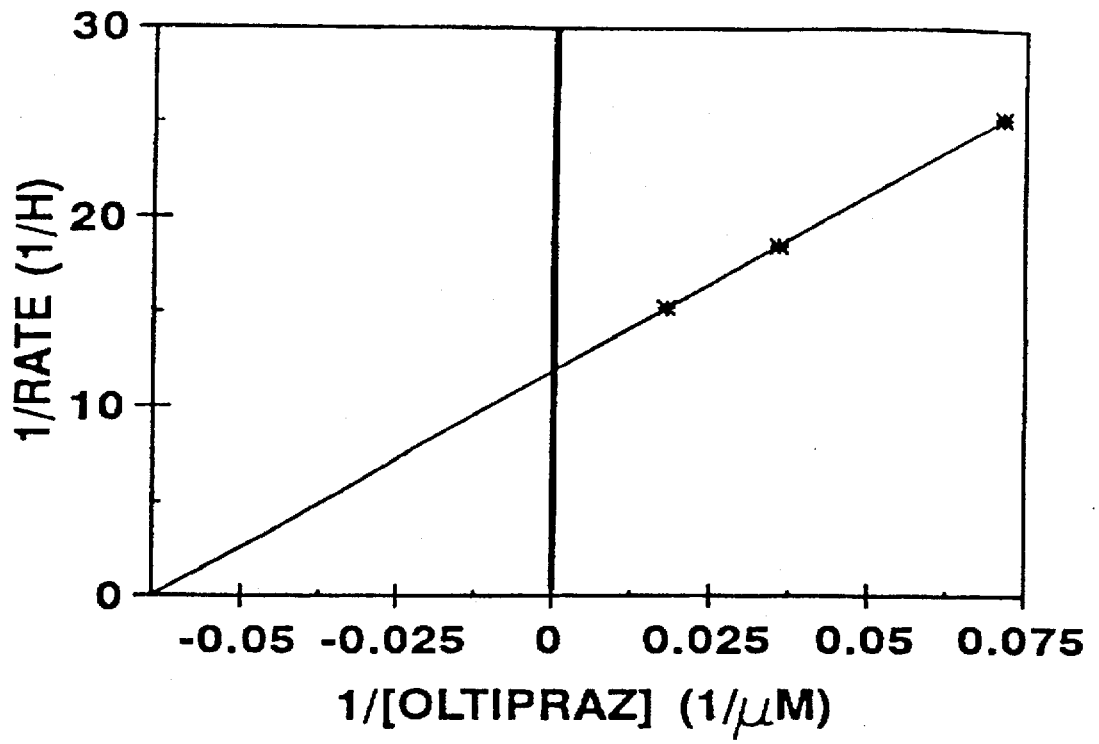
Figure 6C:
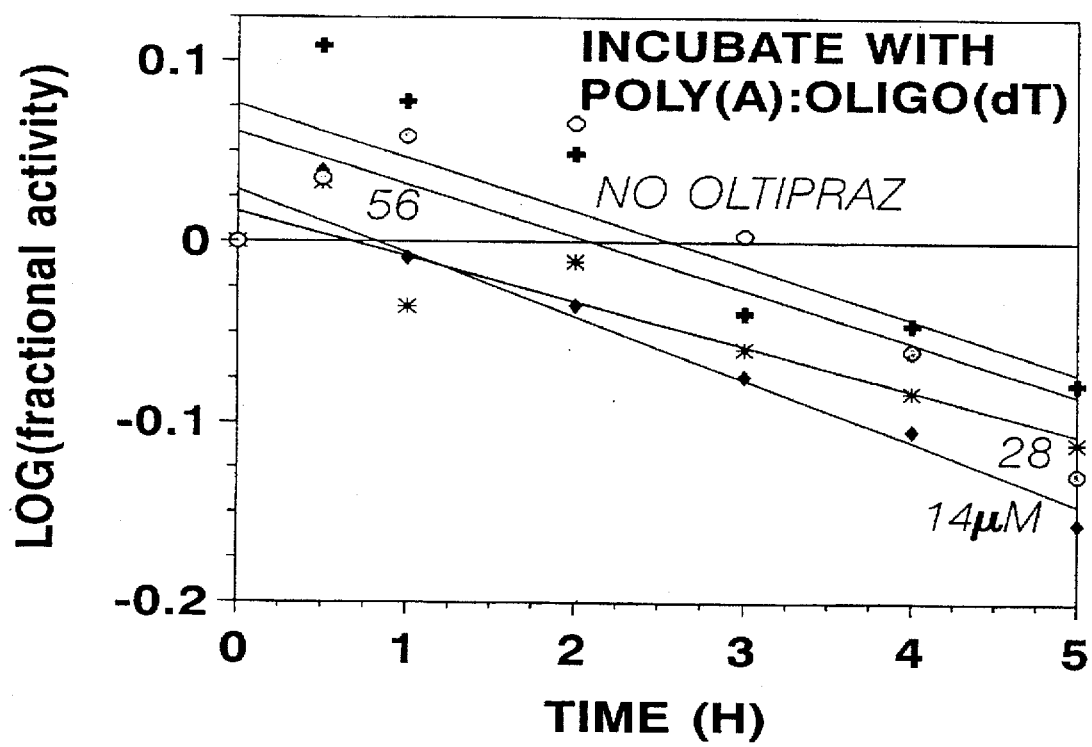
Figure 6D:
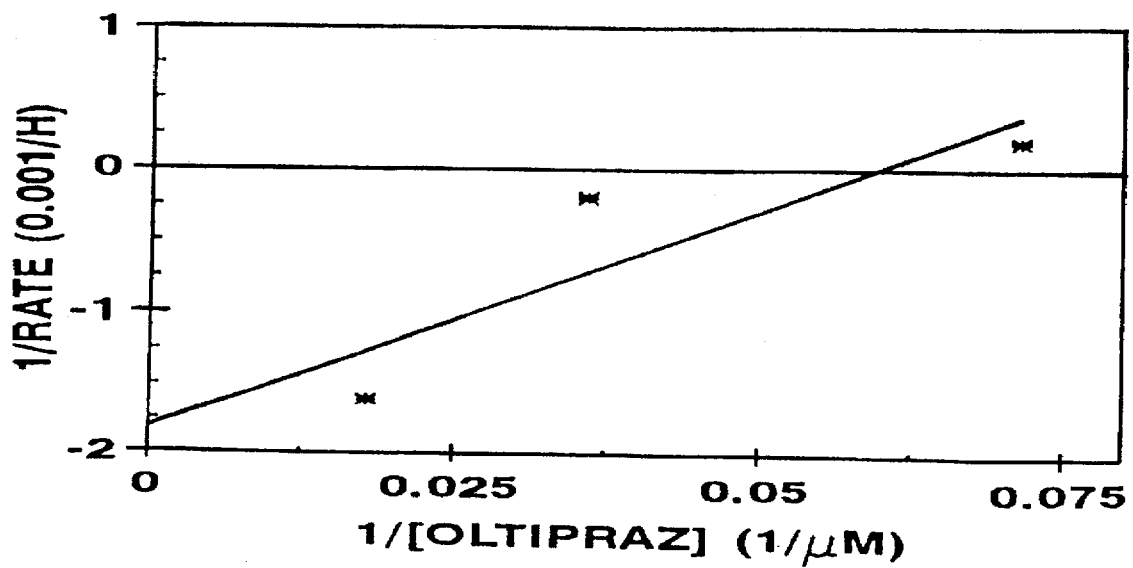

The effect of AZT and oltipraz alone and in combination on HIV-1 replication as determined by IFA and p24 antigen release were examined by the method of Chou and Talalay (27). Typical results are shown in FIG. 4. For the experiment shown, the median doses for AZT and oltipraz were 0.045 and 19.4 µM, respectively. The effect of the combination of oltipraz and AZT at a 300:1 ratio was assessed by utilizing the median dose and the slopes of the median dose plots to generate a combination index plot (Inset FIG. 4; see (27)). At moderate levels of inhibition of p24 release (>37% of positive controls), the effect of oltipraz and AZT was synergistic (combination index <1). This would indicate that the anti-HIV-1 activity of both drugs would be potentiated under conditions of high inhibition of viral replication. Analysis of IFA data also show synergism between the two drugs at high viral inhibition (data not shown). Kong, et al. (31) have recently demonstrated that AZT is synergistic with anti-HIV-1 drugs such as phosphonoformate, and have suggested that combination drug regimens may have a therapeutic advantage.

Example 4

Mechanism of the antiretroviral activity of oltipraz

Oltipraz's unique ability to inhibit HIV-1 replication among anticarcinogenic enzyme inducers tested suggested that an alternative mechanism for inhibition existed. We evaluated the ability of oltipraz to inhibit recombinant HIV-1 reverse transcriptase and found it to be an inhibitor using poly(A):oligo(dT) and TTP as substrates. AZT triphosphate was approximately 1000-fold more potent than oltipraz under identical assay conditions; the closely related congener 1,2-dithiole-3-thione was inactive as an inhibitor of reverse transcriptase. The inhibitory effects of olitpraz on RT was examined in closer detail (FIG. 5). The Dixon plots and their Segal transformations (insets; FIG. 5 see (26)) indicate that oltipraz is a non-competitive inhibitor of RT with respect to TTP ($K_i$=183±50 µM; N=2 experiments) and a mixed inhibitor with respect to poly(A):oligo(dT) ($K_i$= 189±29 µM; N=3 experiments). Moreover, in analogy with our HIV-1 studies in H9 cells, AZT and oltipraz were found to be synergistic inhibitors of reverse transcriptase at moderate to high levels of inhibition (data not shown).

Oltipraz irreversibly inhibits glutathione S-transferases from Schistosoma mansoni, which may be responsible for its antiparasitic activity (38–40). Since oltipraz was a weaker inhibitor of RT in conventional enzyme assays than as an inhibitor of HIV-1 replication, the possibility that it is an irreversible inhibitor of RT was considered. Preincubation of RT with oltipraz (FIG. 6, upper frame) indicated that it behaves kinetically as an irreversible inhibitor of RT ($K_i$= 25.9±3.4 µM; $k_3$=0.0518±0.0089 $h^{-1}$;N=5 independent experiments). The binding site for oltipraz appears to be blocked by template:primer since rates of RT inactivation in the presence of oltipraz are unrelated to its concentration and are indistinguishable from rates of RT inactivation in its absence (FIG. 6, lower frame).

Example 5

Antiretroviral activity of analogs of oltipraz

A large series of oltipraz analogs have been tested for their ability to inhibit HIV-1 replication in H9 cells. Initial screening showed (Table 3) that many compounds possess activity, although most are fairly cytotoxic. However, 4-methyl-5-(2-thiofuranyl)-1,2-dithiole-3-thione was a highly effective inhibitor of HIV-1 replication ($IC_{50}$=1.8±0.7 µM.; N=5 independent experiments). Results also indicate that 4-methyl-5-(2-thiofuranyl)-1,2-dithiole-3-thione also behaves kinetically as an irreversible inhibitor of reverse transcriptase.

Example 6

Effect of oltipraz on HTLV-I

The expression of RT from the supernatants of MT-2 cells (a cell line that is infected with HTLV-I) were measured. Conditions are outlined in the Experimental Details. FIG. 7 shows that oltipraz had a dose-dependent effect on the levels of RT activity found in the media. Thus, oltipraz appears to possess antiviral activity for other members of the retroveridae dose-response characteristics. Bifunctional inducers (29), which require intact Ah receptor function, are inactive. Previously, it had been observed that monofunctional, but not bifunctional inducers, are active in human peripheral mononuclear cells (21). Moreover, the induction patterns between peripheral blood mononuclear cells and H9 cells are virtually identical and suggests that H9 cells represent a useful human model to study anticarcinogenic enzyme inducers. It is interesting to note that basal levels of QR in lymphocytes are quite low in comparison to H9 cells but are significantly higher after treatment with mitogens or immortalization by the Epstein-Barr virus (21). The inducibility of mitogen- or Epstein Barr virus-treated lymphocytes are similar to untreated cells, however, and resemble the data we have obtained with this T-cell lymphoma line.

TABLE 3

1,2-dithiole-3-thione analogs screened

| CATEGORY | # | $R_1$ | $X$ | X | $IC_{50}$ HIV-1 replication (Exp 1) [μM] | $IC_{50}$ HIV-1 replication (Exp 2) [μM] |
|---|---|---|---|---|---|---|
| 5-SUBSTITUTED ANALOGS | 1 | —H | -phenyl | S | Inactive | Inactive |
|  | 2 | —H | -4-methoxyphenyl | S | Inactive | Inactive |
|  | 3 | —H | -2-pyrazinyl | O | 4 | Inactive |
|  | 4 | —H | -2-(5,6-dimethyl)pyrazinyl | S | Inactive | Inactive |
| 5-SUBSTITUTED-4-METHYL ANALOGS | 5 | —CH$_3$ | -2-pyridyl | S | 3 (Toxic) | 10 (Toxic) |
|  | 6 | —CH$_3$ | -3-pyridyl | S | 10 | Inactive |
|  | 7 | —CH$_3$ | -4-pyridyl | S | 60 | 60 |
|  | 8 | —CH$_3$ | -3-pyridazinyl | S | 2 (Toxic) | 4 (Toxic) |
|  | 9 | —CH$_3$ | -2-thiofuranyl | S | 0.4 | 2† |
|  | 10 | —CH$_3$ | -2-(2-pyrazinyl)ethylene | S | Inact.-Tox. | Inact.-Tox. |
| 4-SUBSTITUTED-5-(2-PYRAZINYL) ANALOGS | 11 | —CH$_3$ | -2-pyrazinyl | S | 2 | 3‡ |
|  | 12 | —CH$_3$ | -2-pyrazinyl | O | 10 | Inactive |
|  | 13 | —CH$_2$OH | -2-pyrazinyl | S | 0.4 (Toxic) | 0.2 (Toxic) |
|  | 14 | —CH$_2$CH$_3$ | -2-pyrazinyl | S | 15 (Toxic) | 15 |
|  | 15 | —(CH$_2$)$_3$CH$_3$ | -2-pyrazinyl | S | 2 (Toxic) | 2 (Toxic) |
| MISCELLANEOUS | 16 | —CO$_2$C$_2$H$_5$ | -2-pyridyl | S | 1 (Toxic) | 4 (Toxic) |
|  | 17 | —CO$_2$C$_2$H$_5$ | -4-pyridyl | S | 15 (Toxic) | Inact.-Tox. |
|  | 18 | —Cl | -[4-(2-propyl)phenyl]amino | S | 0.4 (Toxic) | Inact.-Tox. |
|  | 19 | —Cl | -[4-(2-propyl)phenyl]amino | O | Inact.-Tox. | 1 (Toxic) |
|  | 20 | —CH$_2$CO$_2$C$_2$H$_5$ | -5-pyrimidyl | S | Inact.-Tox. | Inact.-Tox. |
|  | 21 | —CH$_2$CON[CH(CH$_3$)$_2$]$_2$ | -5-pyrimidyl | S | 1 (Toxic) | Inact.-Tox. |
|  | 22 | -phenethyl | -3-pyridazinyl | S | 0.4 (Toxic) | Inact.-Tox. |
|  | 23 | —H | -4-pyridyl | * | 0.4 (Toxic) | Inact.-Tox. |
|  | 24 | —(CH$_2$)$_3$CH$_3$ | -3-(6-dimethylamino)pyridazinyl | S | Inactive | Inactive |
| STRUCTURE UNKNOWN | 25 | ???? | ???? | ? | 4 (Toxic) | Inact.-Tox. |
|  | 26 | ???? | ???? | ? | Inact.-Tox. | Inact.-Tox. |

All analogs were evaluated by IFA as described in Experimental Details. Inactive indicates no activity up to 60 μM; toxic indicates that the viability as measured by trypan blue exclusion was low at concentrations at or above IC$_{50}$ to 60 μM.
* = —N—O—(CH$_2$)$_3$N(CH$_3$)$_2$;
†IC$_{50}$ = 1.8 ± 0.7 μM for 5 experiments;
‡IC$_{50}$ = 9.7 ± 2.0 μM for 9 experiments

DISCUSSION

These studies were motivated by published reports that low-molecular weight thiols such as N-acetylcysteine (5,6) and the ester of GSH (6) inhibit HIV-1 replication in cultured cells. It was hypothesized that compounds that could induce a "chemoprotected" state against carcinogens by virtue of increasing levels of GSH and Phase II detoxication enzymes might also protect cells against HIV-1 replication.

The ability of known GSH/Phase II enzyme inducers to elevate levels of GSH and Phase II enzymes in the H9 cutaneous T-cell lymphoma cell line was established first. Prototypical monofunctional inducers (29) of GSH and QR levels in rodent cell lines are active in H9 cells with similar The compounds tested in this study, with the exception of oltipraz and a few other 1,2-dithiole-3-thione compounds, were inactive in inhibiting replication of HIV-1 in H9 cells. It is unclear why exogenous thiols would be able to inhibit HIV-1 replication when inducers of endogenous levels would be inactive, although this in vitro model system is not the same as those utilized by Roederer et al. (5) or Kalibec et al. (6). Pre-treatment of cells with inducers prior to infection (to raise GSH levels) produced no enhancement of the anti-HIV-1 activity of oltipraz, and most of the other compounds tested remained inactive. Perhaps in analogy with these findings, N-acetylcysteine did not alter surrogate markers for HIV-1 in infected patients in a recently reported pharmacokinetics study (32). Thus, this finding, that oltipraz was unique among inducers tested, indicated a novel mechanism by which this compound exerts an antiviral effect. It has been demonstrated that the mechanism of action appears to be due to the irreversible inhibition of reverse transcriptase (i.e., $IC_{50}$ for HIV-1 replication≅$K_i$ for reverse transcriptase inhibition).

Although oltipraz is a relatively weak inhibitor of HIV-1 RT in comparison to other nucleotide and non-nucleotide (including other thiones) inhibitors [review ref. (34)], there are several features of oltipraz which favor further examination of this compound as an anti-HIV-1 agent. First, oltipraz represents a new class of anti-HIV-1 agents. It has been demonstrated that several analogs are also potent inhibitors of HIV-1. Second, oltipraz may be effective in inhibiting other viruses that require reverse transcriptase for part of its replicative life-cycle. Third, oltipraz acts synergistically with AZT in inhibiting the replication of HIV-1. Fourth, oltipraz is used in the treatment of schistosomiasis, and data on the human pharmacology of oltipraz exists (33,35-37). Particularly note that: a) high doses of oltipraz can be tolerated since single or split doses of 20-35 mg/kg are used for the treatment of schistosomiasis (16,17,35); b) Berezin et al. (37) reported that a single 250 mg dose of oltipraz in adults can raise peak serum levels to greater than 1 µg/ml (4 µM). Fifth, oltipraz is under consideration as a potential anticarcinogen in human at high risk for cancer [i.e., in areas where aflatoxin exposure is endemic (14,15, 18)]. Since two AIDS-defining illnesses are Kaposi's sarcoma and lymphoma, it is possible that oltipraz could prevent these diseases by virtue of its anticarcinogenic properties.

In conclusion, inducers of GSH levels do not necessarily inhibit the replication of HIV-1. Oltipraz is highly synergistic with azidothymidine (AZT) at high levels of inhibition of viral replication. The antiretroviral activity of oltipraz appears to be due to its ability to act as an irreversible inhibitor of reverse transcriptase ($K_i$=25.9±3.4 µM; $k_3$=0.0518±0.0089 $h^{-1}$; N=5 independent experiments). Oltipraz behaves synergistically with AZT 5'-triphosphate as an inhibitor of reverse transcriptase. Since oltipraz is synergistic with AZT in inhibiting HIV-1 replication and appears to be well tolerated at anti-HIV-1 doses, oltipraz can play a useful role in the treatment of AIDS.

REFERENCES

1. Eck, H. P., H. Gmunder, M. Hartmann, D. Petzoldt, V. Daniel, and W. Dröge. Low concentrations of acid-soluble thiol (cysteine) in the blood plasma of HIV-1 infected patients. *Biol. Chem. Hoppe Seyler* 370:101–108 (1989).
2. Buhl, R., K. J. Holroyd, A. Mastrangeli, A. M. Cantin, H. A. Jaffe, F. B. Wells, C. Saltini, and R. G. Crystal. Systemic glutathione deficiency in symptom-free HIV-seropositive individuals. *Lancet ii*:1294–1298 (1989).
3. Meister, A. Glutathione deficiency produced by inhibition of its synthesis, and its reversal—Applications in research and therapy. *Pharmacol. Ther.* 51:155–194 (1991).
4. Staal, F. J. T., S. W. Ela, M. Roederer, M. T. Anderson, and L. A. Herzenberg. Glutathione deficiency and Human Immunodeficiency Virus infection. *Lancet* 339:909–912 (1992).
5. Roederer, M., F. J. T Staal, P. A. Raju, S. W. Ela, and L. A. Herzenberg. Cytokine-stimulated human immunodeficiency virus replication is inhibited by N-acetyl-L-cysteine. *Proc. Natl. Acad. Sci.* 87:4884–4888 (1990).
6. Kalebic, T., A. Kinter, G. Poli, M. E. Anderson, A. Meister, and A. S. Fauci. Supression of human immunodeficiency virus expression in chronically infected monocytic cells by glutathione, glutathione ester, and N-acetylcysteine. *Proc. Natl. Acad. Sci.* 88:986–990 (1991).
7. Staal F. J., M. Roederer, and L. A. Herzenberg. Intracellular thiols regulate activation of nuclear factor kappa B and transcription of human immunodeficiency virus. *Proc. Natl. Acad. Sci.* 87:9943–9947 (1990).
8. Dröge, W., H. P. Eck, and S. Mihm. HIV-Induced Cysteine Deficiency and T-Cell Dysfunction—A Rationale for Treatment with N-acetylcysteine. *Immunol. Today* 13:211–214 (1992).
9. Roederer, M., S. W. Ela, F. J. T. Staal, and L. A. Herzenberg. N-Acetylcysteine—A new approach to anti-HIV therapy. *AIDS Res. Hum. Retroviruses* 8:209–217 (1992).
10. Talalay, P., M. J. De Long, and H. J. Prochaska. Molecular mechanisms in protection against carcinogenesis, in *Cancer Biology and Therapeutics* (Cory, J. G., and A. Szentivani). Plenum Press, N.Y., 197–216) (1987).
11. Talalay, P., H. J. Prochaska, and S. R. Spencer. Regulation of enzymes that detoxify the electrophilic forms of chemical carcinogens, in *Xenobiotics and Cancer* (Ernster, L., H. Esumi, Y. Fujii, H. V. Gelboin, R. Kato, and T. Sugimura). Japan Scientific Societies Press/Taylor & Francis, Tokyo/London, 177–187 (1991).
12. Prochaska, H. J., A. B. Santamaria, and P. Talalay. Rapid detection of inducers of enzymes that protect against carcinogens. *Proc. Natl. Acad. Sci USA* 89:2394–2398 (1992).
13. Zhang, Y. S., P. Talalay, C. G. Cho, and G. H. Posner. A major inducer of anticarcinogenic protective enzymes from broccoli—Isolation and elucidation of structure. *Proc. Natl. Acad. Sci* 89:2399–2403 (1992).
14. Kensler, T. W., P. A. Egner, P. M. Dolan, J. D. Groopman, and B. D. Roebuck. Mechanism of protection aginst aflatoxin tumorigenicity in rats fed 5-(2-pyrazinyl)-4-methyl-1,2-dithiol-3-thione (oltipraz) and related 1,2-dithiol-3-thiones and 1,2-dithiol-3-ones. *Cancer Res.* 47:4271–4277 (1987).
15. Roebuck, B. D., Y. L. Liu, A. E. Rogers, J. D. Groopman, and T. W. Kensler. Protection against aflatoxin B1-induced hepatocarcinogenesis in F344 rates by 5-(2-pyrazinyl)-4-methyl-1,2-dithiole-3-thione (oltipraz) :predictive role for short-term molecular dosimetry. *Cancer Res.* 51:5501–5506 (1991).
16. Bella, H., A. G. Rahim, M. D. Mustafa, M. A. Ahmed, S. Wasfi, and J. L. Bennett. Oltipraz—antischistosomal efficacy in Sudanese infected with *Schistosoma mansoni*. *Am. J. Trop. Med. Hyg.* 31:775–778 (1982).
17. Kardaman, M. W., A. Fenwick, A. B. el Igail, M. el Tayeb, J. L. Bennett, and A. A. Daffalla. Field trial with Oltipraz against *Schistosoma mansoni* in the Gezira Irrigated Area, Sudan. *J. Trop. Med. Hyg.* 88:95–100 (1985).
18. Kelloff, G. J., C. W. Boone, W. F. Malone, and V. E. Steele. Chemoprevention clinical trials. *Mutat Res.* 267:291–295 (1992).
19. De Long, M. J., H. J. Prochaska, and P. Talalay. Tissue-specific induction patterns of cancer-protective enzymes in mice by tert-butyl-4-hydroxyanisole and related substituted phenols. *Cancer Res.* 45:546–551 (1985).
20. Prochaska, H. J. and A. B. Santamaria. Direct measurement of NAD(P)H: Quinone reductase from cells cultured in microtiter wells: A screening assay for anticarcinogenic enzyme inducers. *Anal. Biochem.* 169:328–336 (1988).
21. Gordon, G. B., H. J. Prochaska, and L. Y. S. Yang. Induction of NAD(P)H-quinone reductase in human peripheral blood lymphocytes. *Carcinogenesis* 12:2393–2396 (1991).
22. Ellman, G. L. Tissue sulfhydryl groups. *Arch. Biochem. Biophys.* 82:70–77 (1959).

23. Bradford, M. M. A rapid and sensitive method for the quantitation of microgram quantities of protein utilizing the principle of protein-dye binding. *Anal. Biochem.* 72:248–254 (1976).

24. Alley, M. C., C. M. Pacula Cox, M. L. Hursey, L. R. Rubinstein, and M. R. Boyd. Morphometric and colormetric analyses of human tumor cell line growth and drug sensitivity in soft agar culture. *Cancer Res.* 51:1247–1256 (1991).

25. Flexner, C., S. S. Broyles, P. Earl, S. Chakrabarti, and B. Moss. Characterization of human immunodeficiency virus gag/pol gene products expressed by recombinant vaccinia viruses. *Virology* 166:339–349 (1988).

26. Segel, I. H. *Enzyme Kinetics. Behavior and Analysis of Rapid Equilibrium and Steady State Enzyme Systems.* John Wiley & Sons, New York, 100–224 (1975).

27. Chou, T. C. and P. Talalay. Quantitative analysis of dose-effect relationships: The combined effects of multiple drugs or enzyme inhibitors. *Adv. Enz. Regul.* 22:27–55 (1984).

28. De Long, M. J., P. Dolan, A. B. Santamaria, and E. Bueding. 1,2-Dithiol-3-thione analogs: Effects on AND (P)H:quinone reductase and glutathione levels in murine hepatoma cells. *Carcinogenesis* 7:977–980 (1986).

29. Prochaska, H. J. and P. Talalay. Regulatory mechanisms of monofunctional and bifunctional anticarcinogenic enzyme inducers in murine liver. *Cancer Res.* 48:4776–4782 (1988).

30. Twerdok, L. E., S. J. Rembish, and M. A. Trush. Induction of Quinone Reductase and Glutathione in Bone Marrow Cells by 1,2-Dithiole-3-thione—Effect on Hydroquinone-Induced Cytotoxicity. *Toxicol. Appl. Pharmacol.* 112:273–281 (1992).

31. Kong, X. B., Q. Y. Zhu, R. M. Ruprecht, K. A. Watanabe, J. M. Zeidler, J. W. Gold, B. Polsky, D. Armstrong, and T. C. Chou. Synergistic inhibition of human immunodeficiency virus type 1 replication in vitro by two-drug and three-drug combinations of 3'-azido-3'deoxythymidine, phosphonoformate, and 2',3'-dideoxythymidine. *Antimicrob. Agents Chemother.* 35:2003–2011 (1991).

21. Walker, R., H. C. Lane, C. M. Boenning, M. A. Pots, J. A. Kovacs, J. Falloon, R. T. Davey, H. Sussman, L. Gabel, R. Correa-Coronas, H. Masur, and A. S. Fauci. The safety, pharmacokinetics, and antiviral activity of N-acetylcysteine in HIV-infected individuals. *VIII Int. Conf. AIDS* Abstract MoB 0022 (1992). (Abstract).

33. Bieder, A., B. Decouvelaere, C. Gaillard, H. Depaire, D. Heusse, C. Ledoux, M. Lemar, J. P. Le Roy, L. Raynaud, and C. Snozzi. Comparison of the metabolism of oltipraz in the mouse, rat and monkey and in man. Distribution of the metabolites in each species. *Arzneimittel-Forschung.* 33:1289–1297 (1983).

34. Declercq, E., HIV Inhbitors Targeted at the Reverse Transcriptase. *AIDS Res. Hum. Retroviruses* 8:119–137 (1992).

35. Ali, H. M., M. M. Homeida, S. M. Sulaiman, and J. L. Bennett. Diet-controlled blood levels of oltipraz in healthy male subjects. *J. Antimicrob. Chemother.* 13:465–470 (1984).

36. el Igail, A. B., M. el Tayeb, M. W. Kardaman, A. A. Daffalla, H. G. Dixon, and A. Fenwick. Dose-finding trial using Oltipraz to treat schoolchildren infected with *Schistosoma mansoni* in Gezira, Sudan. *J. Trop. Med. Hyg.* 88:101–104 (1985).

37. Berezine, F., M. J. Ratain, and A. B. Benson, III. Pharmacokinetic study of 4-methyl-5-(2-pyrazinyl)-1,2-dithiole-3-thione (oltipraz) in normal volunteers. (Abstract #1244). *Proc. Am. Assoc. Cancer Res.* 33:208 (1992).

38. Nare, B., Smith, J. M., and Prichard, R. K. Differential effects of oltipraz and its oxy-analogue on the viability of Schistosoma-mansoni and the activity of glutathione S-transferase. *Biochem. Pharmacol.* 42:1287–1292 (1991).

39. Nare, B., Smith, J. M., and Prichard, R. K. Oltipraz-induced decrease in the activity of cytosolic glutathione S-transferase in Schistosoma-mansoni. *Int. J. Parasitol.* 21:919–925 (1991).

40. Nare, B., Smith, J. M., and Prichard, R. K. Mechanisms of inactivation of Schistosoma-mansoni and mammalian glutathione S-transferase activity by the antischistosomal drug oltipraz. *Biochem. Pharmacol.* 43: 1345–1351 (1992).

41. Kitz, W. and Wilson, I. B. Esters of methanesulfonic acid as irreversible inhibitors of acetylcholinesterase. *J. Biol. Chem.* 237:3245–3249 (1962).

What is claimed is:

1. A method of inhibiting the replication of a reverse transcriptase-dependent virus which comprises contacting cells infected with a reverse transcriptase-dependent virus with an amount effective to inhibit replication of the reverse transcriptase-dependent virus in the cells, of a 1,2-dithiole-3-thione having the structure:

$$\underset{X}{\overset{Y}{\diagdown}}C=C\underset{\underset{S}{\parallel}}{\overset{S}{\diagdown}}S$$

wherein X is a $C_1$–$C_5$ alkyl group or is —$CH_2COOR$, R being a $C_1$–$C_5$ alkyl group, and wherein Y is a 5- or 6-membered heterocyclic aromatic ring, 1–3 ring atoms of which are nitrogen, oxygen, or sulphur, the remaining ring atoms being carbon.

2. The method of claim 1, wherein the reverse transcriptase-dependent virus is human immunodeficiency virus-1.

3. The method of claim 1, wherein the reverse transcriptase-dependent virus is human immunodeficiency virus-2.

4. The method of claim 1, wherein the reverse transcriptase-dependent virus is feline immunodeficiency virus.

5. The method of claim 1, wherein the reverse transcriptase-dependent virus is feline leukemia virus.

6. The method of claim 1, wherein the reverse transcriptase-dependent virus is human T-cell leukemia virus I.

7. The method of claim 1, wherein the reverse transcriptase-dependent virus is a hepadnavirus.

8. The method of claim 7, wherein the hepadnavirus is hepatitis B virus.

9. The method of claim 2, wherein X is —$CH_3$ and Y is 2-pyrazinyl.

10. The method of claim 2, wherein X is —$CH_3$ and Y is 2-thiofuranyl.

11. The method of claim 2, wherein the infected cells are also contacted with a second inhibitor of replication of human immunodeficiency virus-1.

12. The method of claim 11, wherein the second inhibitor is 3'-azido-3'-deoxythymidine, 2',3'-Dideoxyinosine, 2', 3'-Dideoxycytidine, or 2', 3'-Didehydro-3'-deoxythymidine.

13. The method of claim 12, wherein the second inhibitor is 3'-azido-3'-deoxythymidine.

14. The method of claim 1, wherein the infected cells are T- cells.

15. The method of claim 9, wherein the effective concentration is in the range from about 2.0 µM to about 100.0 µM.

* * * * *